United States Patent [19]
Theobald et al.

[11] 4,171,357
[45] Oct. 16, 1979

[54] CYCLOPROPYLMETHYLPHOSPHORIC ACID DERIVATIVES

[75] Inventors: Hans Theobald; Heinrich Adolphi, both of Limburgerhof; Karl Eicken, Wachenheim, all of Fed. Rep. of Germany

[73] Assignee: BASF Aktiengesellschaft, Fed. Rep. of Germany

[21] Appl. No.: 890,578

[22] Filed: Mar. 20, 1978

Related U.S. Application Data

[63] Continuation of Ser. No. 805,414, Jun. 10, 1977, abandoned.

[30] Foreign Application Priority Data

Jun. 31, 1976 [DE] Fed. Rep. of Germany ....... 2634587

[51] Int. Cl.$^2$ .......................... A01N 9/36; C07F 9/177
[52] U.S. Cl. ...................................... 424/224; 260/958
[58] Field of Search ................ 260/958, 979; 424/224

[56] References Cited

U.S. PATENT DOCUMENTS 2,945,054   7/1960   McCall et al. ...................... 260/958
3,641,223   2/1972   Schlor et al. ..................... 260/979 X Primary Examiner—Anton H. Sutto
Attorney, Agent, or Firm—Keil & Witherspoon

[57] ABSTRACT

New phosphoric acid derivatives, a process for their manufacture by reaction of cyclopropylmethyl halides with salts of phosphoric acid derivatives, and pesticides containing these new phosphoric acid derivatives as active ingredients.

5 Claims, No Drawings

CYCLOPROPYLMETHYLPHOSPHORIC ACID DERIVATIVES

This is a continuation of application Ser. No. 805,414 filed June 10, 1977, now abandoned.

The present invention relates to new phosphoric acid derivatives, a process for their manufacture, and pesticides containing these phosphoric acid derivatives as active ingredients.

The cyclopropylmethylphosphoric acid derivatives according to the invention have the formula

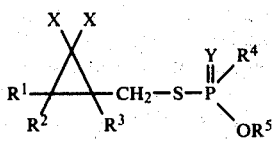

I, where $R^1$, $R^2$ and $R^3$ are identical or different and each denotes hydrogen or linear or branched alkyl of a maximum of 6 carbon atoms, $R^4$ denotes linear or branched alkoxy, alkylthio, alkenylthio or alkynylthio of a maximum of 6 carbon atoms, linear or branched alkyl of a maximum of 3 carbon atoms, phenyl, benzylthio, amino, or linear or branched alkylamino or dialkylamino with a maximum of 5 carbon atoms in the alkyl, $R^5$ denotes linear or branched alkyl of a maximum of 6 carbon atoms, X denotes chlorine or bromine, and Y denotes oxygen or sulfur.

Linear and branched alkyl radicals for $R^1$, $R^2$, $R^3$ and $R^5$ in formula I are methyl, ethyl, propyl, butyl, pentyl and hexyl; alkyl radicals for $R^4$ are methyl, ethyl, propyl and isopropyl; examples of linear or branched alkoxy radicals for $R^4$ are methoxy, ethoxy, propoxy, isopropoxy, butoxy and hexoxy; examples of thio substituents for $R^4$ are methylthio, ethylthio, propylthio, isopropylthio, butylthio, isobutylthio, hexylthio, propenylthio, butene-(2)-thio, hexene-(2)-thio, propyne-(2)-thio and butyne-(2)-thio. Examples of alkylamino and dialkylamino radicals are methyl- and dimethylamino, ethyl- and diethylamino, methylethylamino, isopropylamino, di-n-propylamino, n-butylamino and di-n-butylamino.

Preferred substituents for $R^1$ and $R^2$ are hydrogen, methyl, ethyl, propyl and isopropyl; preferred meanings for $R^3$ are hydrogen and methyl; preferred meanings for $R^5$ are methyl, ethyl, propyl and isopropyl; preferred meanings for $R^4$ are methyl, ethyl, propyl, isopropyl, methoxy, ethoxy, propyloxy, isopropyloxy, methylthio, ethylthio, propylthio, isopropylthio, butylthio, isobutylthio, propenylthio, propynylthio, butynylthio, phenyl, methylamino, ethylamino, propylamino, isopropylamino, dimethylamino, ethylmethylamino and diethylamino.

The present invention also relates to a process for the manufacture of phosphoric acid derivatives of the formula I, wherein cyclopropylmethyl halides of the formula II are reacted with salts of phosphoric acid esters of the formula III to give the phosphoric acid derivatives of the formula I.

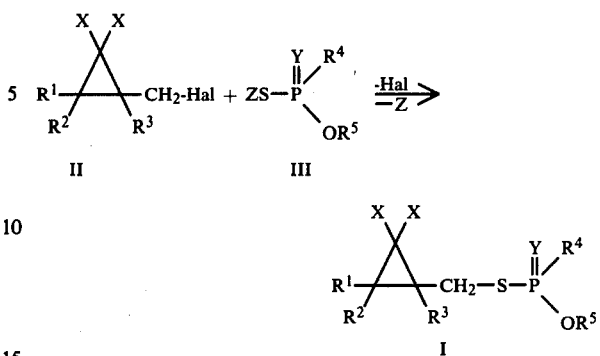

$R^1$, $R^2$, $R^3$, $R^4$, $R^5$, X and Y have the above meanings, Hal denotes halogen and Z denotes an alkali metal ion, an equivalent of an alkaline earth metal ion or an unsubstituted or alkyl-substituted ammonium ion.

Fluorine, chlorine, bromine and iodine are suitable as halogen, chlorine and bromine being preferred. As the alkali metal ions it is preferred to use sodium and potassium, as alkaline earth metal ions magnesium and calcium, and as ammonium ion the unsubstituted ion, methyl-, ethyl-, propyl-, isopropyl-, dimethyl-, diethyl-, trimethyl-, triethyl-, tetramethyl-, and tetraethylammonium.

The reaction is generally carried out in solvents or diluents inert to the reactants. Suitable examples are water, alcohols such as methanol, ethanol and propanol; ethers such as tetrahydrofuran, dioxane and diglycol dimethyl ether; ketones such as acetone, methyl ethyl ketone and diethyl ketone; aromatic hydrocarbons such as toluene, xylenes and chlorobenzene; nitriles such as acetonitrile; dimethylformamide, and dimethyl sulfoxide. Mixtures of these solvents or diluents may also be used. When non-aqueous solvents are used, it may be advantageous to add a catalytic amount of potassium iodide to increase the reactivity.

The starting materials are usually employed in equimolar ratios. In some instances it may be advantageous to use an excess of the one or the other component.

The reaction temperature may be varied within a wide range. Generally, temperatures of from 0° to 150° C., preferably 20° to 100° C., are used.

The cyclopropylmethyl halides of the formula II used as starting materials may be prepared by addition of a carbene of the formula: $CX_2$, X denoting chlorine or bromine, to alkenyl halides, especially chlorides or bromides. The preparation of dichlorocarbene from chloroform is known from Synthesis, 274 et seq., 1974. Dibromocarbene may be prepared analogously from bromoform.

The carbenes may be prepared by conventional methods (Houben-Weyl, Methoden der organischen Chemie, 4/3, 150, 175, 375, 4th ed., Georg Thieme-Verlag, Stuttgart, 1971).

The phosphoric acid salts of the formula III may be prepared by the process described in Houben-Weyl, Methoden der organischen Chemie, 12/2, 131 et seq., Georg Thieme-Verlag, Stuttgart, 1964 or by the process disclosed in German Patent Application No. P 25 06 618.6.

The preparation of the new phosphoric acid derivatives is illustrated by the following examples. Parts by weight bear the same relationship to parts by volume as kilograms to liters.

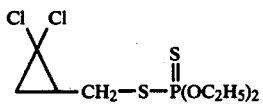

1.

While stirring intensively, 120 parts by volume of 50% aqueous sodium hydroxide solution is dripped into a mixture of 60.5 parts by weight of allyl bromide, 120 parts by weight of chloroform and 1.5 parts by weight of triethylbenzylammonium chloride. The mixture is kept for 3 hours at from 35° to 40° C., and then diluted with water and extracted with chloroform. After drying, the solvent is removed and the residue distilled. There is obtained 36.2 parts by weight of 2,2-dichlorocyclopropylmethyl bromide; yield: 36%; b.p. (25 mm Hg); 79° C.

20.3 parts by weight of ammonium O,O-diethyldithiophosphate in 100 parts by volume of acetonitrile is stirred with 20.4 parts by weight of 2,2-dichlorocyclopropylmethyl bromide and 0.5 part by weight of potassium iodide for 5 hours at from 70° to 80° C. After cooling, the precipitate is suction filtered and the filtrate concentrated. The residue is taken up in toluene, treated with dilute sodium bicarbonate solution and water, and freed from toluene after drying over sodium sulfate. The residue is subjected to incipient distillation at 50° C./0.2 mm Hg. There is obtained 27.6 parts by weight of a pale yellow liquid; yield: 90% of theory.

$C_8H_{15}Cl_2O_2PS_2$ (309)

|  | C | H | S | $Cl_2$ | P |
|---|---|---|---|---|---|
| Calc.: | 31.1 | 4.9 | 20.7 | 22.9 | 10.0 |
| Found: | 31.2 | 4.9 | 20.7 | 23.4 | 10.1 |

60 MHz nmr spectrum in $CDCl_3$ (δ values): 1.36 (6H), 1.5–1.05 (2H), 1.95–2.55 (1H), 3.1 (2H), 3.9–4.5 (4H).

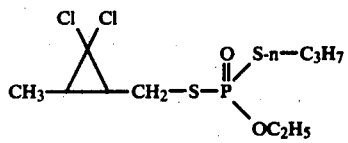

2.

14.7 parts by weight of dimethylammonium O-alkyl-S-n-propyldithiophosphate is stirred with 13.1 parts by weight of 2,2-dichloro-3-methyl-1-methyl bromide in 100 parts by volume of water and 5 parts by volume of dimethylformamide for 6 hours at from 70° to 80° C. After cooling, the precipitated oil is separated and taken up in toluene. The toluene solution is washed with dilute sodium bicarbonate solution and water, and dried over sodium sulfate. After filtering and the removal of toluene, the residue is subjected to incipient distillation at 60° C./0.2 mm Hg. There is obtained 14.5 g of a pale yellow liquid; yield: 72% of theory.

$C_{10}H_{19}Cl_2O_2PS_2$ (337)

|  | C | H | Cl | S | P |
|---|---|---|---|---|---|
| Calc.: | 35.6 | 5.7 | 21.0 | 19.0 | 9.2 |
| Found: | 35.1 | 5.6 | 20.8 | 19.3 | 9.4 |

220 MHz spectrum in $CDCl_3$ (δ values): 0.98 (3H), 1.24 (3H), 1.31 (3H), 1.54 (1H), 1.66 (2H), 1.9 (1H), 2.7 (2H), 2.95 (2H), 3.87 (2H).

The following compounds are obtained analogously:

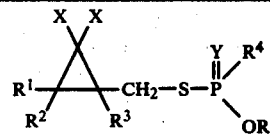

| No. | $R^1$ | $R^2$ | $R^3$ | $R^4$ | $R^5$ | X | Y | nmr data (MHz, 2M): δ values |
|---|---|---|---|---|---|---|---|---|
| 3 | $CH_3$ | H | H | $CH_3O$ | $CH_3$ | Cl | O | (100, $CDCl_3$)1.3(3H), 1.33(1H),1.43(1H), 3.0(2H),3.75(6H) |
| 4 | H | H | $CH_3$ | $C_2H_5O$ | $C_2H_5$ | Cl | S | (60, $CDCl_3$+ DDMSO) 1.25 (6H),1.42 (3H), 1.5 (2H),3.18 (2H), 4.15 (4H) |
| 5 | H | H | H | $i-C_3H_7S$ | $C_2H_5$ | Cl | O | (100 $CDCl_3$)1.26(1H), 1.38 (6H), 1.49 (3H), 1.7 (1H), 2.05 (1H), 3.09 (2H), 3.3–3.7(1H) |
| 6 | H | $CH_3$ | H | $NH-i-C_3H_7$ | $CH_3$ | Cl | O | (100, $CDCl_3$)1.22(6H), 1.4 (2H), 2.96 (2H), 3.2–3.6 (1H + 1H), 3.75 (3H) |
| 7 | $CH_3$ | H | H | $i-C_3H_7S$ | $C_2H_5$ | Cl | O | (100, $CDCl_3$)1.28(3H), 1.33 (3H), 1.4 (3H), 1.5 (3H), 1.1–1.7(2H), 3.05 (2H), 3.55 (1H), 4.21 (2H) |
| 8 | H | H | H | $NH-i-C_3H_7$ | $CH_3$ | Cl | O | (60, $CDCl_3$) 1.1–1.35(6H),1.4(1H), 1.73(1H), 2.05(1H), 2.98(2H),3.3–3.6(1H), 3.76 (3H) |
| 9 | H | H | H | $-C_6H_5$ | $C_2H_5$ | Cl | S | (60, $CDCl_3$),1.4(3H), 2.9(2H),3.8(1H), 4.26(2H),7.2–8.1(5H) |

-continued

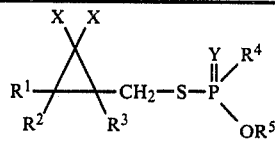

| No. | R¹ | R² | R³ | R⁴ | R⁵ | X | Y | nmr data (MHz, 2M): δ values |
|---|---|---|---|---|---|---|---|---|
| 10 | $CH_3$ | H | H | O-n-$C_3H_7$ | n-$C_3H_7$ | Cl | S | (60,$CDCl_3$),1.0(6H), 1.35(3H), 1.4(1H), 1.5(1H),1.8(4H), 3.1(2H),4.1(4H) |
| 11 | H | H | H | $OCH_3$ | $CH_3$ | Cl | S | (220,$CDCl_3$)1.26(1H), 2.0(2H),2.81(2H), 3.48(6H) |
| 12 | H | H | H | S—$CH_2$—C₆H₅ | $C_2H_5$ | Cl | O | (60,$CDCl_3$),1.3(3H), 1.71(1H),3.0(2H), 3.98(2H),4.2(2H), 7.24(5H) |
| 13 | H | H | H | $OCH_3$ | $CH_3$ | Cl | O | (100,$CDCl_3$),1.31(1H), 1.73(1H),1.96(1H), 3.06(2H),3.8(6H) |
| 14 | $CH_3$ | H | H | $CH_3$—C≡C—$CH_2$—S | $C_2H_5$ | Cl | O | (60,$CDCl_3$)1.1–1.66 (3 + 3 + 2),1.78(3H), 2.8–3.3(2H),3.4–3.8 (2H),4.0–4.5(2H) |
| 15 | H | H | H | n-$C_3H_7$O | n-$C_3H_7$ | Cl | O | (60,$CDCl_3$),0.91(6H), 1.3(1H),1.66(4H), 1.81(2H),3.0(2H), 4.02(4H) |
| 16 | H | H | H | $CH_3$S— | $C_2H_5$ | Cl | O | (60,$CDCl_3$),1.33(1H), 1.4(3H),1.8(1H), 2.08(1H),2.4(3H), 3.12(2H),4.3(2H) |
| 17 | H | H | H | n-$C_3H_7$S— | $C_2H_5$ | Cl | O | (100,$CDCl_3$),1.04(3H), 1.32(1H),1.44(3H), 1.6–1.9(2 + 1H), 2.08(1H),2.75–3.3 (4H),4.28(2H) |
| 18 | $CH_3$ | H | H | $C_2H_5$O | $C_2H_5$ | Cl | S | (60,$CDCl_3$),1.3(3H), 1.4(6H),1.9(1H), 3.1(2H),4.25(4H) |
| 19 | $CH_3$ | H | H | $CH_3$O | $CH_3$ | Cl | S | (220,$CDCl_3$),1.22(3H), 1.88(1H),1.76(1H), 2.1(2H),3.46(6H) |
| 20 | $CH_3$ | H | H | —N($CH_3$)$_2$ | $CH_3$ | Cl | O | (60,$CDCl_3$),1.38(3H), 1.4(1H),1.5(1H), 2.8(6H),3.05(2H), 3.8(3H) |
| 21 | $CH_3$ | H | H | S—$CH_2$—C₆H₅ | $C_2H_5$ | Cl | O | (60,$CDCl_3$),1.3(3H), 1.4(3H),1.5(1H), 1.8(1H),3.0(2H), 4.4(4H) |
| 22 | H | H | H | —S—$CH_2$—CH($CH_3$)$_2$ | $C_2H_5$ | Cl | O | (60,$CDCl_3$),1.0(6H), 1.2–1.5(2H),1.38(3H), 1.5–2.1(1 + 1H), 2.5–3.3(2 + 2H), 3.9–4.4(2H) |
| 23 | H | $CH_3$ | H | —S—$CH_2$—CH($CH_3$)$_2$ | $C_2H_5$ | Cl | O | (60,$CDCl_3$),1.1(6H), 1.18–1.55(2 + 3 + 3H), 1.6–2.15(1H),2.54–3.1/2 + 2H),3.95–4.33(2H) |
| 22 | $CH_3$ | $CH_3$ | H | S—n-$C_3H_7$ | $C_2H_5$ | Br | O | |
| 23 | $CH_3$ | H | H | S—i-$C_3H_7$ | $C_2H_5$ | Br | O | |
| 24 | $CH_3$ | H | H | —N($CH_3$)$_2$ | $C_2H_5$ | Cl | O | |
| 25 | H | H | H | $NH_2$ | $C_2H_5$ | Cl | O | |

The phosphoric acid derivatives of the formula I according to the invention have a better insecticidal and nematocidal action than prior art compounds having a similar scope of action. Furthermore, the new compounds have a very low toxicity to warmbloods. They may be used for combatting sucking and biting insects, mites, and especially plant-parasitic nematodes. Either the pests or the objects to be protected against pest attack may be treated with an effective amount of one or more of the active ingredients according to the invention.

The main representatives of the sucking insects are aphids (Aphidae) such as *Myzus persicae, Doralis fabae, Rhopalosiphum padi., Microsiphum pisi, Macrosiphum*

*solanifolii, Cryptomyzus korschelti, Sapaphis mali, Hyalopterus arundinis* and *Myzus cerasi*, and bugs such as *Piesma quadratum, Dysdercus intermedius, Cimex lectularius, Rhodnius prolixus* and *Triatoma infestans.*

The most important of the biting insects are Lepidoptera such as *Plutella maculipennis, Lymantria dispar., Euproctis chrysorrhoea* and *Malacosoma neustria,* further *Mamestra brassicae, Agrotis segetum, Pieris brassicae, Hyponomeuta padella, Ephestia kühniella* and *Galleria mellonella.*

Other representatives of biting insects are beetles (Coleoptera) such as *Sitophilus granarius, Leptinotarsa decemlineata, Dermestes frischi, Tribolium castaneum, Calandra* or *Sitophilus zeamais, Stegobium paniceum, Tenebrio molitor,* including soil-borne species such as wireworms (Agriotes spec.) and cockchafers (*Melolontha melolontha*), cockroaches such as *Blatella germanica, Periplaneta americana, Blatta orientalis, Blaberus giganteus, Blaberus fuscus,* and *Henschoutedenia flexivitta;* Orthoptera, e.g., *Acheta domestica,* termites such as *Reticulitermes flavipes,* and Hymenoptera such as ants, e.g., *Lasius niger.*

Of the mites (Acari) particular importance attaches to spider mites (Tetranychidae) such as *Tetranychus telaris* (=*Tetranychus althaeae* or *Tetranychus urticae*) and *Paratetranychus pilosus* (=*Panonychus ulmi*); gall mites, e.g., *Eriophyes ribis,* and Tarsonemidae, e.g., *Hemitarsonemus latus* and *Tarsonemus pallidus;* and finally ticks such as *Ornithodorus moubata.*

Examples of nematodes are root-knot nematodes such as *Meloidogyne incognita, Meloidogyne hapla, Meloidogyne javanica,* cyst-forming nematodes such as *Heterodera rostochiensis, Heterodera schachtii, Heterodera avenae, Heterodera glycines, Heterodera trifolii,* stem and leaf eelworms such as *Ditylenchus dipsaci, Ditylenchus destructor, Pratylenchus neglectus, Pratylenchus penetrons, Pratylenchus goodeyi, Pratylenchus curvitatus,* and *Tylenchorhynchus dubius, Tylenchorhynchus claytoni, Rotylenchus robutus, Heliocotylenchus multicintus, Radopholus similis, Belonolaimus longicaudatus, Longidorus elongatus, Trichodorus primitivus.*

Application of the active ingredients may be effected for instance in the form of directly sprayable solutions, powders, suspensions, dispersions, emulsions, oil dispersions, pastes, dusts, broadcasting agents, or granules by spraying atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use liquors may vary within a wide range; it is generally from 0.0001 and 10%, preferably from 0.01 to 1%.

The active ingredients may also be successfully used in the ultra-low volume method, where it is possible to apply formulations containing up to 95% of active ingredient, or even the 100% active ingredient.

An example of a possible formulation is given below:
500 g of O-ethyl-S-n-propyl-S-2,2-dichlorocyclopropylmethylphosphorus dithionate
40 g of calcium dodecylbenzene sulfonate
60 g of alkoxylated fatty acid amide
xylene makeup to 1,000 ml.

There may be added to the individual active ingredients or mixtures thereof (if desired, immediately before use (tankmix)) oils of various types, herbicides, fungicides, insecticides and bactericides.

These agents may be added to the compounds of the invention in weight ratios of from 1:10 to 10:1.

Examples of active ingredients which may be admixed are as follows:
O,O-dimethyl-O-(p-nitrophenyl)-phosphorothioate
O,O-diethyl-O-(p-nitrophenyl)-phosphorothioate
O-ethyl-O-(p-nitrophenyl)-phenylphosphonothioate O,O-dimethyl-O-(3-methyl-4-nitrophenyl)-phosphorothioate
O,O-diethyl-O-(2,4-dichlorophenyl)-phosphorothioate
O-ethyl-O-(2,4-dichlorophenyl)-phenylphosphonothioate
O,O-dimethyl-O-(2,4,5-trichlorophenyl)-phosphorothioate
O-ethyl-O-(2,4,5-trichlorophenyl)-ethylphosphonothioate
O,O-dimethyl-O-(4-bromo-2,5-dichlorophenyl)-phosphorothioate
O,O-dimethyl-O-(2,5-dichloro-4-iodophenyl)-phosphorothioate
O,O-dimethyl-O-(3-methyl-4-methylthiophenyl)-phosphorothioate
O-ethyl-O-(3-methyl-4-methylthiophenyl)-isopropyl-phosphoramidate
O,O-diethyl-O-[p-(methylsulfinyl)-phenyl]-phosphorothioate
O-ethyl-S-phenylethylphosphonodithioate
O,O-diethyl-[2-chloro-1-(2,4-dichlorophenyl)-vinyl]-phosphate
O,O-dimethyl-[2-chloro-1-(2,4,5-trichlorophenyl)]-vinyl phosphate
O,O-dimethyl-S-(1-phenyl)-ethyl acetate phosphorodithioate
bis-(dimethylamino)-fluorophosphine oxide
octamethylpyrophosphoramide
O,O,O,O-tetraethyldithiopyrophosphate
S-chloromethyl-O,O-diethylphosphorodithioate
O-ethyl-S,S-dipropylphosphorodithioate
O,O-dimethyl-O-2,2-dichlorovinyl phosphate
O,O-dimethyl-1,2-dibromo-2,2-dichloroethyl phosphate
O,O-dimethyl-2,2,2-trichloro-1-hydroxyethylphosphonate
O,O-dimethyl-S-[1,2-biscarbethoxyethyl-(1)]-phosphorodithioate
O,O-dimethyl-O-(1-methyl-2-carbomethoxyvinyl)-phosphate
O,O-dimethyl-S-(N-methylcarbamoylmethyl)-phosphorodithioate
O,O-dimethyl-S-(N-methylcarbamoylmethyl)-phosphorothioate
O,O-dimethyl-S(N-methoxyethylcarbamoylmethyl)-phosphorodithioate
O,O-dimethyl-S-(N-formyl-N-methylcarbamoylmethyl)-phosphorodithioate
O,O-dimethyl-O-[1-methyl-2-(methylcarbamoyl)-vinyl]-phosphate
O,O-dimethyl-O-[(1-methyl-2-dimethylcarbamoyl)-vinyl]-phosphate
O,O-dimethyl-O-[(1-methyl-2-chloro-2-diethylcarbamoyl)-vinyl]-phosphate
O,O-diethyl-S-(ethylthiomethyl)-phosphorodithioate
O,O-diethyl-S-[(p-chlorophenylthio)-methyl]-phosphorodithioate
O,O-dimethyl-S-(2-ethylthioethyl)-phosphorothioate
O,O-dimethyl-S-(2-ethylthioethyl)-phosphorodithioate
O,O-dimethyl-S-(2-ethylsulfinylethyl)-phosphorothioate
O,O-diethyl-S-(2-ethylthioethyl)-phosphorodithioate
O,O-dimethyl--(2-ethylsulfinylethyl)-phosphorothioate
O,O-diethylthiophosphoryliminophenylacetonitrile
O,O-diethyl-S-(2-chloro-1-phthalimidoethyl)-phosphorodithioate
O,O-diethyl-S-[6-chlorobenzoxazolon-(2)-yl-(3)]-methyldithiophosphate
O,O-dimethyl-S-[2-methoxy-1,3,4-thiodiazol-5-onyl-(4)-methyl]-phosphorodithioate
O,O-diethyl-O-[3,5,6-trichloropyridyl-(2)]-phosphorothioate
O,O-diethyl-O-(2-pyrazinyl)-phosphorothioate
O,O-diethyl-O-[2-isopropyl-4-methylpyrimidinyl-(6)]-phosphorothioate
O,O-diethyl-O-[2-(diethylamino)-6-methyl-4-pyrimidinyl]-thionophosphate
O,O-dimethyl-S-(4-oxo-1,2,3-benzotriazin-3-ylmethyl)-phosphorodithioate
O,O-dimethyl-S-[(4,6-diamino-1,3,5-triazin-2-yl)-methyl]-phosphorodithioate
O,O-diethyl-(1-phenyl-1,2,4-triazol-3-yl)-thionophosphate
O,S-dimethylphosphoramidothioate
O,S-dimethyl-N-acetylphosphoramidothioate
γ-hexachlorocyclohexane
1,1-di-(p-methoxyphenyl)-2,2,2,-trichloroethane
6,7,8,9,10,10-hexachloro-1,5,5a,6,9,9a-hexahydro-6,9-methano-2,4,3-benzodioxathiepine-3-oxide
1,2-dibromo-3-chloropropane
1,3-dichloropropene
1,3-dichloropropene+1,2-dichloropropane
1,2-dibromoethane
2-sec-butylphenyl-N-methylcarbamate
o-chlorophenyl-N-methylcarbamate
3-isopropyl-5-methylphenyl-N-methylcarbamate
o-isopropoxyphenyl-N-methylcarbamate
3,5-dimethyl-4-methylmercaptophenyl-N-methylcarbamate
4-dimethylamino-3,5-xylyl-N-methylcarbamate
2-(1,3-dioxolan-2-yl)-phenyl-N-methylcarbamate
1-naphthyl-N-methylcarbamate
2,3-dihydro-2,2-dimethylbenzofuran-7-yl-N-methylcarbamate
2,2-dimethyl-1,3-benzodioxol-4-yl-N-methylcarbamate
2-dimethylamino-5,6-dimethyl-4-pyrimidinyldimethylcarbamate
2-methyl-2-(methylthio)-propionaldehyde-O-(methylcarbamoyl)-oxime
S-methyl-N-[(methylcarbamoyl)-oxy]-thioacetimidate
methyl-N',N'-dimethyl-N-[(methylcarbamoyl)-oxy]-1-thiooxamidate
N-(2-methyl-4-chlorophenyl)-N',N'-dimethylformamidine
tetrachorothiophene The biological action of the compounds of the invention is illustrated by the following examples.

EXAMPLE 1

Breeding experiment with cotton stainers (*Dysdercus intermedius*)

250 g of sterile sandy oil is thoroughly mixed with 20 ml of aqueous active ingredient emulsion and 1 liter beakers are filled with the soil prepared in this manner. 20 Dysdercus larvae in the penultimate stage are then introduced into each beaker. The animals are fed on cotton seeds swollen in water. Observation is continued until the larvae of the next generation emerge.

| Compound no. | Amount of compound in sand in ppm | Mortality in % |
|---|---|---|
| 1 | 5 | 100 |
| 4 | 10 | 100 |
| 11 | 2.5 | considerable inhibition |
| 12 | 10 | considerable inhibition |
| 14 | 5 | 100 |

-continued

| Compound no. | Amount of compound in sand in ppm | Mortality in % |
| --- | --- | --- |
| 16 | 5 | 100 |
| 18 | 10 | 100 |
| 19 | 2.5 | 100 |

EXAMPLE 2

Contact action and effect of ingested food on caterpillars of the diamondback moth (*Plutella maculipennis*)

Leaves of young cabbage plants are dipped for 3 seconds into aqueous emulsions containing the active ingredient in different concentrations. After excess liquid has been briefly allowed to drip off, the leaves are placed on a moistened filter paper in a Petri dish. 10 caterpillars of the 4th stage are then placed on each leaf. The mortality rate is determined after 48 hours.

| Compound no. | Concentration of active ingredient emulsion in % | Mortality in % |
| --- | --- | --- |
| 16 | 0.01 | 100 |
|  | 0.005 | 85 |

EXAMPLE 3

Contact action on ticks (*Ornithodorus moubata*)

Young ticks having a diameter of from 1.5 to 2 mm are placed in tissue paper bags which are then dipped for 5 seconds in test emulsions of various concentrations. The bags are then suspended at 22° C. The animals surviving after 48 hours are counted.

| Compound no. | Active ingredient concentration in % | Mortality rate in % |
| --- | --- | --- |
| 17 | 0.1 | 100 |
|  | 0.04 | 80 |
| 11 | 0.1 | 100 |
| 12 | 0.04 | 100 |
| 14 | 0.1 | 100 |
| 16 | 0.1 | 100 |

EXAMPLE 4

Action on root-knot nematodes (*Meloidogyne incognita*), soil treatment

Soil heavily infested with nematodes is split into 200 g portions which are intimately mixed with 30 ml of aqueous active ingredient formulations and filled into plastic pots. Two cucumber seeds are then placed in the soil prepared in this manner. The experiments are carried out under greenhouse conditions. After 6 weeks root attack is assessed.

| Compound no. | Amount of active ingredient in soil in ppm | |
| --- | --- | --- |
| 2 | 150 | no attack |
| 17 | 150 | no attack |
| 11 | 150 | slight attack |
| 16 | 150 | no attack |

EXAMPLE 5

Tomato plants are planted in soil heavily infested with *Meloidogyne incognita* and left for 14 days. They are then removed from the soil, and the roots are rinsed and dipped for 60 minutes in aqueous active ingredient formulations of various concentrations. The plants are then planted in sterilized compost and root attack is assessed after 6 weeks.

| Compound no. | Concentration of active ingredient formulation in % | |
| --- | --- | --- |
| 2 | 0.01 | no attack |
| 17 | 0.0025 | no attack |

EXAMPLE 6

Action on beet nematodes (*Heterodera schachtii*)

Soil heavily infested with beet nematodes is intimately mixed with the test agent and filled into 4-compartment vessels made of transparent plastic. 4 seeds of the rape variety "Diament" are placed in each vessel. The agent used for comparison purposes is 2,3-dihydro-2,2-dimethylbenzofuran-7-yl-N-methylcarbamate.

The roots are examined for cysts after 8 weeks.

| Compound no. | Amount of active ingredient in soil in ppm | |
| --- | --- | --- |
| 2 | 50.0 | no cysts |
| 17 | 25.0 | no cysts |
| Comparative agent | 100 | occasional cysts |

We claim:

1. Phosphoric acid derivatives of the formula $$\begin{array}{c} X \ X \\ R^1 \diagup\hspace{-0.5em}\diagdown \\ R^2 \ R^3 \end{array}\!\!-CH_2-S-\underset{OR^5}{\overset{\overset{\displaystyle Y}{\|}}{P}}\!\!-R^4 \qquad I,$$

where $R^1$, $R^2$ and $R^3$ are identical or different and each denotes hydrogen or linear or branched alkyl of a maximum of 6 carbon atoms, $R^4$ denotes linear or branched alkoxy, alkylthio, alkenylthio or alkynylthio of a maximum of 6 carbon atoms, linear or branched alkyl of a maximum of 3 carbon atoms, phenyl, benzylthio, amino, or linear or branched alkylamino or dialkylamino with a maximum of 5 carbon atoms in the alkyl, $R^5$ denotes linear or branched alkyl of a maximum of 6 carbon atoms, X denotes chlorine or bromine, and Y denotes oxygen or sulfur.

2. A method of combatting pests, wherein the pests or the objects to be protected against pest attack are treated with an effective amount of a phosphoric acid derivative of formula I of claim 1.

3. O-ethyl-S-n-propyl-S-methyl-2,2-dichlorocyclopropylmethylphosphorodithioate.

4. O-ethyl-S-n-propyl-S-2,2-dichlorocyclopropylmethylphosphorodithioate.

5. A pesticide containing a solid or liquid carrier and a phosphoric acid derivative of formula I of claim 1 as active component.

* * * * *